United States Patent [19]

Grundei

[11] Patent Number: 4,648,842
[45] Date of Patent: Mar. 10, 1987

[54] IMPLANT REPLACEMENT FOR A EXTRACTED TOOTH

[75] Inventor: Hans Grundei, Lübeck, Fed. Rep. of Germany

[73] Assignee: S + G Implants GmbH, Lübeck, Fed. Rep. of Germany

[21] Appl. No.: 775,759

[22] Filed: Sep. 13, 1985

[30] Foreign Application Priority Data

Sep. 19, 1984 [DE] Fed. Rep. of Germany ....... 3434309

[51] Int. Cl.⁴ .............................................. A61C 13/00
[52] U.S. Cl. .................................................... 433/175
[58] Field of Search ......................... 433/173, 175, 176

[56] References Cited

U.S. PATENT DOCUMENTS 3,979,828  9/1976  Taylor ................................. 433/175
4,051,598 10/1977  Sneer .................................. 433/175

Primary Examiner—Robert Peshock
Attorney, Agent, or Firm—Balogh, Osann, Kramer, Dvorak, Genova & Traub

[57] ABSTRACT

The implant comprises a molding which consists of a metal having an open-cell structure permitting bone tissue to grow in with subsequent formation of bone in the cells and which is provided with an upper conical recess for insertion of an adhesion cone to be fixed in the recess by static friction. The cone is provided on one side with a flattening which comes into contact with a corresponding wall part of the recess in the implant, the cone being connected or connectable to the replacement tooth.

1 Claim, 5 Drawing Figures

IMPLANT REPLACEMENT FOR A EXTRACTED TOOTH

BACKGROUND OF THE INVENTION

1. Field of the Invention

The invention relates to an implant replacement for an extracted tooth, consisting of a conical metallic molding which can be inserted into the jaw bone and can be connected to a replacement tooth by means of a part protruding from the jaw.

2. Description of the Prior Art

Hitherto known implants of the abovementioned type consist of a body-compatible metal, ceramics or a mixture of ceramics and alumina. Attempts have here been made to improve the connection of the implant surface to the bone by means of bone tissue growing in, in such a way that, for example, the implant surface was roughened, which generally required machining on the implant surface after the preparation of the molding. Due to the small dimensions of the implants, it was accordingly in general only possible to obtain a small roughening of or formation of lacunas in the implant surface, so that the growth of bone tissue with subsequent formation of bone, for making a better connection between the jaw bone and the implant, was very limited.

OBJECTS AND SUMMARY OF THE INVENTION

It is the object of the invention to make possible, on the one hand, a perfect irreleasable connection of the implant to the jaw bone and, on the other hand, a simple, rapid connection of the implant to the replacement tooth.

According to the invention, this object is achieved when the molding, which consists in a known manner of a metal having an open-cell structure permitting bone tissue to grow in with formation of bone in the cells, is provided with an upper conical recess for insertion of a cone which is fixed by static friction in the recess and has on one side a flattening which comes into contact with a corresponding wall part of the recess and is connected or connectable to the replacement tooth.

By this means, after insertion of the implant into the prepared jaw bone, the formation of bone tissue and growth into the cells with subsequent formation of bone is stimulated and accelerated by the sharp edges of the open-cell structure of the implant which thus forms an irreleasable unit with the jaw bone after a relatively short time. Owing to the conical recess in the implant, it is possible rapidly and simply to obtain, due to the static friction, a firm connection to an insertable cone to which the replacement tooth is connected or which, with an upward-pointing cone, engages into a corresponding conical recess in the replacement tooth, likewise by static friction. In this case, twisting of the cone in the implant is prevented by providing the cone on one side with a flattening and providing the recess in the implant with a projection which matches the flattening and comes into contact with it.

To ensure effective static friction of the cone insertable into the implant in every case, it can be advantageous to bound the conical recess in the implant by a thin solid metal wall which is fused to the open-cell metal of the implant. The cone then bears with increased friction against an areal boundary of the recess.

BRIEF DESCRIPTION OF THE DRAWINGS

The invention will now be explained, by way of example, with reference to the accompanying partly diagrammatic drawings, in which.

DETAILED DESCRIPTION OF THE PREFERRED EMBODIMENTS

Figure 1:
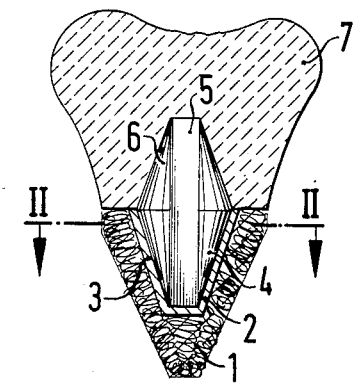
FIG. 1 is a vertical section through the implant according to the invention, with a connected replacement tooth.
Figure 2A:
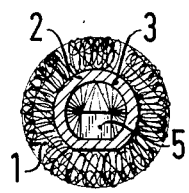
FIG. 2a is a cross-section through the implant along line II—II of FIG. 1, without an inserted cone.
Figure 2B:
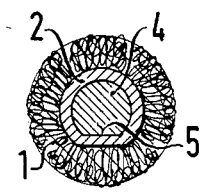
FIG. 2b is the same cross-section as FIG. 2a, but with the inserted cone.

The implant according to the invention consists of a molding 1 having an open-cell metal structure, the cells of which permit bone tissue to grow in with subsequent formation of spongy bone. This implant is provided with a conical recess 3 which advantageously is bounded by a thin solid metal wall 2 fused to the implant material. Into this conical recess 3, a mounting or adhesion cone 4 can be inserted which, by static friction, makes a firm connection to the boundary face of the recess 3 or to the metal wall 2. This cone 4 is provided on one side with a flattening 5, which comes into contact with a corresponding wall part of the implant, whereby twisting of the cone 4 in the implant 1 is avoided.

Figure 3:
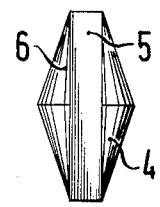
FIG. 3 is a side view of the cone according to FIG. 1.

According to the example, FIGS. 1 and 3, the cone 4 is connected to an upward-pointing support cone 6 which likewise engages in a corresponding conical recess in the replacement tooth 7 to make a firm connection by static friction.

Figure 4:
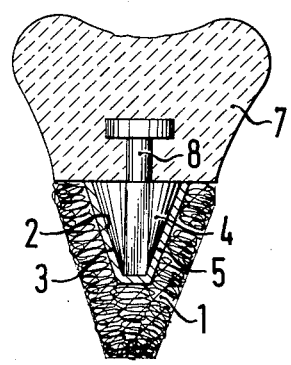
FIG. 4 is a section, corresponding to FIG. 1, with a modified connection of the cone to the replacement tooth.

It is also possible to connect the replacement tooth 7 to the cone 4 by an anchorage 8 (FIG. 4), so that it is only necessary to connect the replacement tooth 7 connected to the cone 4 rapidly and firmly by central insertion into the conical recess 3 in the implant 1.

While the invention and many of its attendant advantages will be understood from the foregoing description and it will be apparent that various changes may be made in the form, construction and arrangement of the parts without departing from the spirit and scope of the invention of sacrificing all of its material advantages, the form hereinbefore described merely being a preferred embodiment thereof.

What is claimed is:

1. An implant as a replacement for an extracted tooth, the implant comprising a molding implantable in a jaw bone, and having at one end an essentially conical recess with a flat surface formed by a solid metal wall, and having at its other end other end an open cell structure connected to said metal wall to permit bone tissue to grow thereinto following implantation, and a metal cone both ends of which are conical with a flat surface, and one end of which is inserted into said conical recess of said molding and the other end of which is engageable with a replacement tooth.

* * * * *